(12) United States Patent
Lee et al.

(10) Patent No.: US 8,859,531 B2
(45) Date of Patent: Oct. 14, 2014

(54) PHARMACEUTICAL COMPOSITION INCLUDING MOMETASONE FUROATE AND AZELASTINE HYDROCHLORIDE FOR NASAL ADMINISTRATION

(75) Inventors: Sang-Yong Lee, Gyeonggi-do (KR); Geun-Hyeog Lee, Gyeonggi-do (KR); Byong-Sun Choi, Seoul (KR); Jong-Hyeon Ryu, Gyeonggi-do (KR); Jin-Ha Park, Gyeonggi-do (KR); Mi-Jin O, Gyeonggi-do (KR)

(73) Assignee: Hanlim Pharmaceutical Co., Ltd, Gyeonggi-Do (KR)

( * ) Notice: Subject to any disclaimer, the term of this patent is extended or adjusted under 35 U.S.C. 154(b) by 0 days.

(21) Appl. No.: 13/990,373

(22) PCT Filed: Nov. 18, 2011

(86) PCT No.: PCT/KR2011/008826
§ 371 (c)(1),
(2), (4) Date: May 29, 2013

(87) PCT Pub. No.: WO2012/074231
PCT Pub. Date: Jun. 7, 2012

(65) Prior Publication Data
US 2013/0252929 A1    Sep. 26, 2013

(30) Foreign Application Priority Data
Nov. 29, 2010  (KR) .................. 10-2010-0119632

(51) Int. Cl.
*A01N 45/00*    (2006.01)
*A61K 31/56*    (2006.01)
*A61K 31/58*    (2006.01)
*A61K 31/573*   (2006.01)
*A61K 31/55*    (2006.01)

(52) U.S. Cl.
CPC ............... *A61K 31/58* (2013.01); *A61K 31/573* (2013.01); *A61K 31/55* (2013.01)
USPC ........................................................ 514/171

(58) Field of Classification Search
None
See application file for complete search history.

(56) References Cited

U.S. PATENT DOCUMENTS

| | | | |
|---|---|---|---|
| 5,164,194 A | 11/1992 | Hettche | |
| 6,117,864 A * | 9/2000 | Morita et al. | 514/217.05 |
| 6,576,677 B1 | 6/2003 | Ukai et al. | |
| 8,071,073 B2 | 12/2011 | Dang et al. | |
| 8,163,723 B2 | 4/2012 | Lulla et al. | |
| 8,168,620 B2 | 5/2012 | Lulla et al. | |
| 2006/0025391 A1 | 2/2006 | Lulla et al. | |
| 2006/0110331 A1* | 5/2006 | Dang et al. | 424/45 |
| 2007/0020330 A1 | 1/2007 | Dang et al. | |
| 2009/0238771 A1 | 9/2009 | Berry et al. | |
| 2009/0291143 A1 | 11/2009 | Lulla et al. | |
| 2009/0312724 A1* | 12/2009 | Pipkin et al. | 604/294 |
| 2009/0318397 A1 | 12/2009 | Lulla et al. | |
| 2010/0099650 A1 | 4/2010 | Knauer | |
| 2010/0152147 A1 | 6/2010 | Fuge et al. | |
| 2010/0331289 A1 | 12/2010 | Lulla et al. | |

FOREIGN PATENT DOCUMENTS

JP    2010138125 A  *  6/2010
WO    97/01337 A1      1/1997

* cited by examiner

*Primary Examiner* — Dennis Heyer
*Assistant Examiner* — Daniel M Podgorski
(74) *Attorney, Agent, or Firm* — Vorys, Sater, Seymour and Pease LLP; Mihsun Koh

(57) ABSTRACT

The present invention provides a pharmaceutical composition for nasal administration comprising mometasone furoate and azelastine hydrochloride, wherein the pharmaceutical composition comprises thaumatin as an agent for reducing bitterness and irritation.

16 Claims, No Drawings

PHARMACEUTICAL COMPOSITION INCLUDING MOMETASONE FUROATE AND AZELASTINE HYDROCHLORIDE FOR NASAL ADMINISTRATION

TECHNICAL FIELD

The present invention relates to a pharmaceutical composition for nasal administration comprising mometasone furoate and azelastine hydrochloride. More specifically, the present invention relates to a pharmaceutical composition whose nasal sensation is improved by reducing bitterness and irritation of azelastine hydrochloride through the use of thaumatin.

BACKGROUND ART

Mometasone furoate, one of the steroids used for treating allergic rhinitis, is known to be highly effective in prolonged symptom-relief. Azelastine hydrochloride, one of the short-acting antihistamines, is known to be highly effective in immediate symptom-improvement. Therefore, co-administration of these two drugs in a combination formulation is expected to exhibit an excellent effect in the long-term treatment of allergic rhinitis, along with immediate symptomatic improvement.

International Publication WO97/01337 has disclosed a nasal spray or nasal drop formulation comprising azelastine or its salt; and beclomethasone, flunisolide, triamcinolone, dexamethasone or budesonide. And also, International Publication WO2003/105856 has disclosed a pharmaceutical formulation suitable for nasal or ocular administration (e.g., a nasal spray), which comprises azelastine or its salt; and a steroid such as mometasone furoate.

Meanwhile, azelastine hydrochloride has strong bitter taste. The degree of the bitter taste is so intense that it is even found to be unpleasant in a dilution of $1 \times 10^6$ time (U.S. Pat. No. 5,164,194). After azelastine hydrochloride is intranasally applied, such a bitterness of azelastine hydrochloride is delivered to the pharynx, thereby causing unpleasant taste and irritation. U.S. Pat. No. 6,576,677 has disclosed a use of polyvinylpyrrolidone and/or copovidone for alleviating the unpleasant taste of azelastine hydrochloride. And also, International Publication WO2006/058022 has disclosed a pharmaceutical composition comprising azelastine hydrochloride and mometasone furoate, wherein sucralose is used as an agent for masking bitterness.

DISCLOSURE

Technical Problem

The present invention provides a pharmaceutical composition for nasal administration comprising mometasone furoate and azelastine hydrochloride, the nasal sensation of which is improved by reducing bitterness and irritation of azelastine hydrochloride through the use of thaumatin extracted from a natural source, i.e., *Thaumatococcus daniellii* Benth.

That is, it is an object of the present invention to provide a pharmaceutical composition for nasal administration comprising mometasone furoate and azelastine hydrochloride, in which thaumatin is used as an agent for reducing bitterness and irritation.

Technical Solution

In accordance with an aspect of the present invention, there is provided a pharmaceutical composition for nasal administration comprising mometasone furoate and azelastine hydrochloride, wherein the pharmaceutical composition comprises thaumatin as an agent for reducing bitterness and irritation.

In the pharmaceutical composition for nasal administration according to the present invention, the thaumatin may be present in an amount ranging from 0.1 to 0.5 w/v %.

In an embodiment of the present invention, there is provided a pharmaceutical composition comprising 0.01 to 1.0 w/v % of mometasone furoate; 0.05 to 1.0 w/v % of azelastine hydrochloride; 0.1 to 0.5 w/v % of thaumatin; 1.0 to 5.0 w/v % of a thickening agent; 0.2 to 0.6 w/v % of a buffering agent; 0.001 to 0.1 w/v % of a surfactant; 5.0 to 10.0 w/v % of an isotonic agent; 0.01 to 1.0 w/v % of a stabilizer; and 0.002 to 0.05 w/v % of a preservative, in an aqueous medium. In a preferable embodiment, there is provided a pharmaceutical composition consisting of 0.05 w/v % of mometasone furoate; 0.14 w/v % of azelastine hydrochloride; 0.25 w/v % of thaumatin; 2.0 w/v % of a mixture of microcrystalline cellulose and sodium carboxymethyl cellulose; 0.2 w/v % of citric acid; 0.28 w/v % of sodium citrate; 0.01 w/v % of polyoxyethylene sorbitan monooleate; 2.1 w/v % of glycerin; 6.6 w/v % of sorbitol; 0.1 w/v % of sodium edetate; 0.02 w/v % of benzalkonium chloride; and the remaining amount of water.

The pharmaceutical composition may be administered preferably in a nasal spray form.

Advantageous Effects

It has been found by the present invention that thaumatin effectively reduces the bitterness and irritation of azelastine hydrochloride, thereby providing excellent nasal sensation when intranasally administered. Therefore, patients' drug compliance can be increased by formulating mometasone furoate and azelastine hydrochloride through the use of thaumatin as an agent for reducing bitterness and irritation; and then administering the resulting formulation intranasally. In addition, the pharmaceutical composition for nasal administration comprising mometasone furoate and azelastine hydrochloride, which is formulated with thaumatin according to the present invention, has excellent stability.

BEST MODE

The present invention provides a pharmaceutical composition for nasal administration comprising mometasone furoate and azelastine hydrochloride, wherein the pharmaceutical composition comprises thaumatin as an agent for reducing bitterness and irritation.

Said "thaumatin" is a protein mixture obtained by extracting the seed of *Thaumatococcus daniellii* Benth (plant of West Africa) with water and then purifying the extract. The protein mixture comprises 5 proteins, i.e., thaumatin I, II, III, a, and b, mainly thaumatin I and II. Thaumatin I and II have the almost same amino acid sequences. Thaumatin is listed in the Korea Food Additives Code; and being used in ices, refreshing beverages, etc., as a sweetening or flavor agent. It is known that thaumatin is a protein produced against the attack of viroid pathogens. Thaumatins exhibit an inhibitory activity against the hypha growh and sporulation of fungi.

It has been found by the present invention that thaumatin effectively reduces the bitterness and irritation of azelastine hydrochloride, thereby providing excellent nasal sensation when intranasally administered. In the pharmaceutical composition according to the present invention, the thaumatin may be present in an amount ranging from 0.1 to 0.5 w/v %, preferably from 0.2 to 0.4 w/v %, more preferably about 0.25 w/v %, based on total volume of the composition.

In the pharmaceutical composition for nasal administration according to the present invention, mometasone furoate, one of the active ingredients, may be present in an amount ranging from 0.01 to 1.0 w/v %, preferably in an amount ranging from 0.05 to 0.5 w/v %, more preferably in an amount of about 0.05 w/v %, based on total volume of the composition. And also, azelastine hydrochlorid, another active ingredient, may be present in an amount ranging from 0.05 to 1.0 w/v %, preferably in an amount ranging from 0.1 to 0.5 w/v %, more preferably in an amount of about 0.14 w/v %, based on total volume of the composition.

The pharmaceutical composition for nasal administration according to the present invention may include excipients conventionally used in formulations for nasal administration, such as thickening agents, buffering agents, surfactants, isotonic agents, stabilizers, preservatives, etc.

As a thickening agent, a mixture of microcrystalline cellulose and sodium carboxymethyl cellulose (for example, Avicel RC 591, Avicel RC 581, Avicel CL 611, etc.) may be used. The thickening agent may be used in an amount ranging from 1.0 to 5.0 w/v %, preferably in an amount ranging from 1.0 to 4.0 w/v %, more preferably in an amount of about 2.0 w/v %, based on total volume of the composition, although the amount thereof varies according the thickening agent used.

As a buffering agent, a combination of acid and its salt (for example, a combination of citric acid and sodium citrate) may be used. The buffering agent may be used in an amount ranging from 0.2 to 0.6 w/v %, preferably in an amount ranging from 0.3 to 0.5 w/v %, based on total volume of the composition, although the amount thereof varies according the buffering agent used, buffer strength, etc. In an embodiment, a combination of about 0.2 w/v % of citric acid (or its hydrate) and 0.28 w/v % of sodium citrate (or its hydrate), based on total volume of the composition, may be used.

A surfactant facilitates the suspension of mometasone furoate, one of the sparingly water-soluble drugs. As a surfactant, polyoxyethylene sorbitan monooleate (for example, Polysorbate 40, Polysorbate 60, Polysorbate 80, etc.) may be used. The surfactant may be used in an amount ranging from 0.001 to 0.1 w/v %, preferably in an amount ranging from 0.005 to 0.05 w/v %, more preferably in an amount of about 0.01 w/v %, based on total volume of the composition, although the amount thereof varies according the buffering agent used.

As an isotonic agent, glycerin, sorbitol, or a combination of glycerin and sorbitol may be used. Since the use of saccharides can additionally provide sweet taste, saccharides (such as sorbitol) may be preferably used. The isotonic agent may be used in an amount ranging from 5.0 to 10.0 w/v %, preferably in an amount ranging from 6.0 to 9.0 w/v %, based on total volume of the composition, although the amount thereof varies according the isotonic agent used. In an embodiment, a combination of about 2.1 w/v % of glycerin and 6.6 w/v % of sorbitol (e.g., D-sorbitol), based on total volume of the composition, may be used.

As a stabilizer, sodium edetate or its hydrate may be used. The stabilizer may be used in an amount ranging from 0.01 to 1.0 w/v %, preferably in an amount of about 0.1 w/v %, based on total volume of the composition. In addition, as a preservative, conventional preservatives such as benzalkonium chloride may be used in an amount ranging from 0.002 to 0.05 w/v %, preferably in an amount of about 0.02 w/v, based on total volume of the composition.

In an embodiment of the present invention, there is provided a pharmaceutical composition for nasal administration comprising 0.01 to 1.0 w/v % of mometasone furoate; 0.05 to 1.0 w/v % of azelastine hydrochloride; 0.1 to 0.5 w/v % of thaumatin; 1.0 to 5.0 w/v % of a thickening agent; 0.2 to 0.6 w/v % of a buffering agent; 0.001 to 0.1 w/v % of a surfactant; 5.0 to 10.0 w/v % of an isotonic agent; 0.01 to 1.0 w/v % of a stabilizer; and 0.002 to 0.05 w/v % of a preservative, in an aqueous medium (for example, purified water etc.).

In another embodiment of the present invention, there is provided a pharmaceutical composition for nasal administration comprising 0.01 to 1.0 w/v % of mometasone furoate; 0.05 to 1.0 w/v % of azelastine hydrochloride; 0.1 to 0.5 w/v % of thaumatin; 1.0 to 5.0 w/v % of a mixture of microcrystalline cellulose and sodium carboxymethyl cellulose; 0.2 to 0.6 w/v % of a mixture of citric acid and sodium citrate; 0.001 to 0.1 w/v % of polyoxyethylene sorbitan monooleate; 5.0 to 10.0 w/v % of a mixture of glycerin and sorbitol; 0.01 to 1.0 w/v % of sodium edetate; and 0.002 to 0.05 w/v % of benzalkonium chloride, in an aqueous medium (for example, purified water etc.).

In preferable embodiment of the present invention, there is provided a pharmaceutical composition for nasal administration consisting of 0.05 w/v % of mometasone furoate; 0.14 w/v % of azelastine hydrochloride; 0.25 w/v % of thaumatin; 2.0 w/v % of a mixture of microcrystalline cellulose and sodium carboxymethyl cellulose; 0.2 w/v % of citric acid; 0.28 w/v % of sodium citrate; 0.01 w/v % of polyoxyethylene sorbitan monooleate; 2.1 w/v % of glycerin; 6.6 w/v % of sorbitol; 0.1 w/v % of sodium edetate; 0.02 w/v % of benzalkonium chloride; and the remaining amount of water.

The pharmaceutical composition for nasal administration according to the present invention may be administered preferably in a nasal spray form. Therefore, the pharmaceutical composition of the present invention may be formulated preferably into a nasal spray form.

The present invention will be described in further detail with reference to the following examples. These examples are for illustrative purposes only and are not intended to limit the scope of the present invention.

Examples 1 and 2

Suspensions for Nasal Spray

Suspensions for nasal spray were prepared according to the components and amounts shown in Table 1 below. Each amount of Table 1 refers to an amount in w/v %.

Avicel RC 591 and glycerin were dispersed in sterile purified water with a Homo Mixer (Mixture I). In a separate vessel, azelastine hydrochloride, benzalkonium chloride, citric acid hydrate, sodium citrate hydrate, sodium edetate hydrate, D-sorbitol and thaumatin were dissolved in sterile purified water under stirring the mixture (Mixture II). In a separate vessel, mometasone furoate and Polysorbate 80 were dispersed in sterile purified water (Mixture III). The mixture I was mixed with the mixture II under stirring; and the resulting mixture was then mixed with the mixture III under stirring. Sterile purified water was added to the resulting mixture, to adjust the final volume.

TABLE 1

| Component | Example 1 | Example 2 |
| --- | --- | --- |
| Mometasone furoate EP | 0.05 | 0.05 |
| Azelastine hydrochloride EP | 0.14 | 0.14 |
| Avicel RC 591 NF | 2.0 | 2.0 |
| Glycerin USP | 2.1 | 2.1 |
| Sodium edetate hydrate KP | 0.1 | 0.1 |
| Citric acid hydrate KP | 0.2 | 0.2 |
| Sodium citrate hydrate KP | 0.28 | 0.28 |
| Polysorbate 80 KP | 0.01 | 0.01 |
| Benzalkonium chloride KP | 0.02 | 0.02 |
| D-sorbitol USP | 6.6 | 6.6 |
| Thaumatin KPC | 0.25 | 0.125 |
| Sterile purified water KP | Remaining amount (adjusted to 100%) | Remaining amount (adjusted to 100%) |

Comparative Examples 1 to 3

Suspensions for nasal spray were prepared according to the components and amounts shown in Table 2 below, using various artificial sweetening agents instead of thaumatin, in the same manner as in Example 1. Each amount of Table 2 refers to an amount in w/v %.

TABLE 2

| Component | Comparative Example 1 | Comparative Example 2 | Comparative Example 3 |
| --- | --- | --- | --- |
| Mometasone furoate EP | 0.05 | 0.05 | 0.05 |
| Aazelastine hydrochloride EP | 0.14 | 0.14 | 0.14 |
| Avicel RC 591 NF | 2.0 | 2.0 | 2.0 |
| Glycerin USP | 2.1 | 2.1 | 2.1 |
| Sodium edetate hydrate KP | 0.1 | 0.1 | 0.1 |
| Citric acid hydrate KP | 0.2 | 0.2 | 0.2 |
| Sodium citrate hydrate KP | 0.28 | 0.28 | 0.28 |
| Polysorbate 80 KP | 0.01 | 0.01 | 0.01 |
| Bbenzalkonium chloride KP | 0.02 | 0.02 | 0.02 |
| D-sorbitol USP | 6.6 | 6.6 | 6.6 |
| Neohesperidin | 0.25 | — | — |
| Sucralose NF | — | 0.25 | — |
| Acesulfame potassium | — | — | 0.25 |
| Sterile purified water KP | Remaining amount (adjusted to 100%) | Remaining amount (adjusted to 100%) | Remaining amount (adjusted to 100%) |

Experimental Example 1

Evaluation of Nasal Sensation

Nasal sensation was evaluated based on the 4 items, i.e., "bitterness felt", "sweetness felted", "irritation", and "persistence of irritation". The evaluation grades of each item were assigned 1 to 5 from 'weak' to 'strong'. That is, in the items of "bitterness felt", "sweetness felted", or "irritation", the evaluation grade '1' means "weak bitterness was felt", "weak sweetness was felted", or "there was weak irritation", while the evaluation grade '5' means "strong bitterness was felt", "strong sweetness was felted", or "there was strong irritation". And also, in the item of "persistence of irritation", the evaluation grade '1' means "irritation was persisted shortly", while the evaluation grade '5' means "irritation was persisted for long duration".

Each suspension prepared in Example 1 and Comparative Examples 1 to 3 was filled into a vessel for nasal spray; and then intranasally sprayed to 30 volunteers for 10 seconds. The evaluation of nasal sensation regarding the above items was performed; and the results thereof are shown in Table 3 below. The results of Table 3 refer to a mean value of the evaluation grades in each item.

TABLE 3

| | Bitterness felt | Sweetness felt | Irritation | Persistence of irritation |
| --- | --- | --- | --- | --- |
| Example 1 | 2.1 | 3.9 | 1.8 | 1.9 |
| Comparative Example 1 | 4.2 | 2.2 | 3.2 | 1.8 |
| Comparative Example 2 | 2.4 | 4.5 | 3.2 | 3.1 |
| Comparative Example 3 | 2.9 | 4.2 | 3.4 | 3.6 |

As seen from the results of Table 3, the composition containing thaumatin according to the present invention showed almost no bitterness and relatively strong sweetness; and also showed excellent properties especially in the irritation item and the persistence-of-irritation item. The composition containing neohesperidin, which is one of the artificial sweetening agents, (i.e., Comparative Example 1) showed very poor masking effects against the bitter taste and irritation derived from azelastine hydrochloride. And also, the composition containing sucralose (i.e., Comparative Example 2) showed relatively good bitterness-masking effects, but very poor irritation-masking effects. The composition containing acesulfame potassium (i.e., Comparative Example 3) showed not only very poor irritation-masking effects, but also persisted-irritations for long duration. Therefore, it can be seen that the composition containing thaumatin according to the present invention exhibits excellent nasal sensation, in comparison with those containing other sweetening agents.

Experimental Example 2

Mucosal Irritation Tests

Irritancy tests on the ocular mucosa were carried out as a mucosal irritation test, because the ocular mucosa is more sensitive to irritation than the nasal mucosa; and the well established-test method thereof makes it easy to interpret the results. The tests were carried out in accordance with the internal management protocol (10-BL-455 protocol). The preparation of this protocol and the test-performing were conducted in accordance with the Guideline on Toxicity Study of Drugs (No. 2009-116, KFDA, 4 Aug. 2009), the Good Laboratory Practice (No. 2009-183, KFDA, 22 Dec. 2009), and the OECD Principles of Good Laboratory Practice (1997). The suspension of Example 1 was administered to the ocular mucosa of New Zealand White rabbits, in a dose of 0.1 mL/head; and then the symptoms thereof were observed for 7 days.

The results were as follows: (1) any general symptom(s) and animal death associated with the application of the test material was not observed during the test period; (2) any body weight change associated with the application of the test material was not observed during the test period; (3) any change was not observed in both the eye-washing group and non-eye-washing group, as a result of the observation of ocular reaction after the application of the test material; (4) the Index of Acute Ocular Irritation (I.A.O.I) was evaluated as zero (i.e., non-irritant) during the test period, as a result of the observation of ocular reaction after the application of the test material.

tained under the conditions of 20±5° C. and 60% relative humidity for 24 months. Appearance was observed with the naked eyes; and the pH was measured with a pH meter. Both the quantitative analyses of azelastine hydrochloride and its degradation products and the quantitative analyses of mometasone furoate and its degradation products were carried out with a high-performance liquid chromatography (HPLC), under the following HPLC conditions:

<HPLC Conditions for Quantitative Analyses of Azelastine Hydrochloride and Its Degradation Products>
Column: Capcellpak $C_{18}$ Column (4.6×250 mm, 5 μm)
Column Temperature: 30° C.
Detector: UV spectrophotometer (wavelength: 212 nm)
Mobile phase: prepared by adding 941.1 mg of sodium 1-hexanesulfonate to 1 L of 40% acetonitrile solution.

<HPLC Conditions for Quantitative Analyses of Mometasone Furoate and Its Degradation Products>
Column: Capcellpak $C_{18}$ Column (4.6×150 mm, 5 μm)
Column Temperature: 30° C.
Detector: UV spectrophotometer (wavelength: 254 nm)
Mobile phase: a mixed solvent of water and acetonitrile (50/50)

The results of stability tests according to long-term storage under the conditions of 20±5° C. and 60% relative humidity for 24 months are shown in Table 4 below.

TABLE 4

|  | Criteria | Initial | 3 months | 6 months | 9 months | 12 months | 18 months | 24 months |
|---|---|---|---|---|---|---|---|---|
| Appearance | White non-transparent suspension | The same as on the left | The same as on the left | The same as on the left | The same as on the left | The same as on the left | The same as on the left | The same as on the left |
| pH | 4.0-6.0 | 4.67 | 4.65 | 4.60 | 4.57 | 4.55 | 4.51 | 4.49 |
| Azelastine hydrochloride |  |  |  |  |  |  |  |  |
| Degradation product | Degradation products A, B, C: not more than 0.2% | Not detected | Not detected | Not detected | Not detected | Not detected | Not detected | Not detected |
|  | Unknown maximum degradation product: not more than 0.2% | 0.01% | 0.01% | 0.01% | 0.01% | 0.01% | 0.02% | 0.02% |
|  | Total degradation products: not more than 1.0% | 0.01% | 0.01% | 0.01% | 0.01% | 0.01% | 0.02% | 0.02% |
| Contents | 90.0-110.0% of the labeled amount | 99.2% | 100.3% | 100.1% | 100.0% | 99.4% | 99.6% | 100.0% |
| Mometasone furoate |  |  |  |  |  |  |  |  |
| Degradation product | Unknown maximum degradation product: not more than 0.1% | 0.02% | 0.02% | 0.03% | 0.03% | 0.03% | 0.05% | 0.05% |
|  | Total degradation products: not more than 0.6% | 0.02% | 0.02% | 0.03% | 0.03% | 0.03% | 0.05% | 0.05% |
| Contents | 90.0-110.0% of the labeled amount | 99.7% | 99.3% | 99.6% | 99.7% | 99.5% | 99.4% | 99.6% |

Therefore, the pharmaceutical composition prepared according to the present invention was found to be non-irritant, when applied to the ocular mucosa; and therefore it was also found that it would not cause any irritation, even when applied to the nasal cavity.

Experimental Example 3

Physical and Chemical Stability Tests (1) Long-Term Storage Test
Stability tests according to long-term storage were carried out, while the suspension prepared in Example 1 was main- From the results of Table 4, it can be seen that the composition of the present invention has excellent physical and chemical stabilities for 24 months.

(2) Accelerated Tests
Accelerated tests were carried out, while the suspension prepared in Example 1 was maintained under the conditions of 40° C. and 75% relative humidity for 6 months. The observation of appearance, the pH measurement, the quantitative analyses of azelastine hydrochloride and its degradation products, and the quantitative analyses of mometasone furoate and its degradation were performed in the same manners as in the above (1). The results are shown in Table 5 below.

TABLE 5

|  | Criteria | Initial | 1 month | 3 months | 6 months |
|---|---|---|---|---|---|
| Appearance | White non-transparent suspension | The same as on the left | The same as on the left | The same as on the left | The same as on the left |
| pH | 4.0-6.0 | 4.67 | 4.62 | 4.53 | 4.48 |
| Azelastine hydrochloride | | | | | |
| Degradation product | Degradation products A, B, C: not more than 0.2% | Not detected | Not detected | Not detected | Not detected |
|  | Unknown maximum degradation product: not more than 0.2% | 0.01% | 0.01% | 0.02% | 0.02% |
|  | Total degradation products: not more than 1.0% | 0.01% | 0.01% | 0.02% | 0.04% |
| Contents | 90.0-110.0% of the labeled amount | 99.2% | 100.3% | 99.7% | 99.1% |
| Mometasone furoate | | | | | |
| Degradation product | Unknown maximum degradation product: not more than 0.1% | 0.02% | 0.03% | 0.03% | 0.05% |
|  | Total degradation products: not more than 0.6% | 0.02% | 0.04% | 0.04% | 0.06% |
| Contents | 90.0-110.0% of the labeled amount | 99.7% | 99.4% | 99.2% | 99.0% |

From the results of Table 5, it can be seen that the composition of the present invention also has excellent physical and chemical stabilities in the accelerated test for 6 months.

The invention claimed is:

1. A pharmaceutical composition for nasal administration comprising mometasone furoate, azelastine hydrochloride and thaumatin, wherein azelastine hydrochloride is an amount of from 0.05 to 1.0 w/v % and thaumatin is an amount of from 0.1 to 0.5 w/v %, based on the total volume of the composition, and thaumatin reduces the bitterness and irritation caused by azelastine.

2. The pharmaceutical composition for nasal administration of claim 1, wherein the pharmaceutical composition comprises 0.01 to 1.0 w/v % of mometasone furoate; 0.05 to 1.0 w/v % of azelastine hydrochloride; 0.1 to 0.5 w/v % of thaumatin; 1.0 to 5.0 w/v % of a thickening agent; 0.2 to 0.6 w/v % of a buffering agent; 0.001 to 0.1 w/v % of a surfactant; 5.0 to 10.0 w/v % of an isotonic agent; 0.01 to 1.0 w/v % of a stabilizer; and 0.002 to 0.05 w/v % of a preservative, in an aqueous medium.

3. The pharmaceutical composition for nasal administration of claim 2, wherein the pharmaceutical composition comprises 0.01 to 1.0 w/v % of mometasone furoate; 0.05 to 1.0 w/v % of azelastine hydrochloride; 0.1 to 0.5 w/v % of thaumatin; 1.0 to 5.0 w/v % of a mixture of microcrystalline cellulose and sodium carboxymethylcellulose; 0.2 to 0.6 w/v % of a mixture of citric acid and sodium citrate; 0.001 to 0.1 w/v % of polyoxyethylene sorbitan monooleate; 5.0 to 10.0 w/v % of a mixture of glycerin and sorbitol; 0.01 to 1.0 w/v % of sodium edetate; and 0.002 to 0.05 w/v % of benzalkonium chloride, in an aqueous medium.

4. The pharmaceutical composition for nasal administration of claim 3, wherein the pharmaceutical composition consists of 0.05 w/v % of mometasone furoate; 0.14 w/v % of azelastine hydrochloride; 0.25 w/v % of thaumatin; 2.0 w/v % of a mixture of microcrystalline cellulose and sodium carboxymethyl cellulose; 0.2 w/v % of citric acid; 0.28 w/v % of sodium citrate; 0.01 w/v % of polyoxyethylene sorbitan monooleate; 2.1 w/v % of glycerin; 6.6 w/v % of sorbitol; 0.1 w/v % of sodium edetate; 0.02 w/v % of benzalkonium chloride; and the remaining amount of water.

5. The pharmaceutical composition for nasal administration according claim 4, wherein the pharmaceutical composition is a nasal spray form.

6. The pharmaceutical composition for nasal administration according to claim 1, wherein the pharmaceutical composition is a nasal spray form.

7. The pharmaceutical composition for nasal administration according to claim 2, wherein the pharmaceutical composition is a nasal spray form.

8. The pharmaceutical composition for nasal administration according claim 3, wherein the pharmaceutical composition is a nasal spray form.

9. A method of reducing the bitterness and irritation caused by azelastine hydrochloride in a pharmaceutical composition for nasal administration comprising active ingredients of mometasone furoate and azelastine hydrochloride, the method comprising administering the pharmaceutical composition to a subject in need thereof in combination with thaumatin in the composition, wherein azelastine hydrochloride is an amount of from 0.05 to 1.0 w/v % and thaumatin is an amount of from 0.1 to 0.5 w/v % based on the total volume of the composition.

10. The method of claim 9, wherein the pharmaceutical composition comprises 0.01 to 1.0 w/v % of mometasone furoate, 0.05 to 1.0 w/v % of azelastine hydrochloride, 0.1 to 0.5 w/v % of thaumatin, 1.0 to 5.0 w/v % of a thickening agent, 0.2 to 0.6 w/v % of a buffering agent, 0.001 to 0.1 w/v % of a surfactant, 5.0 to 10.0 w/v % of an isotonic agent, 0.01 to 1.0 w/v % of a stabilizer and 0.002 to 0.05 w/v % of a preservative, in an aqueous medium.

11. The method of claim 10, wherein the pharmaceutical composition is a nasal spray form.

12. The method of claim 10, wherein the pharmaceutical composition is a nasal spray form.

13. The method of claim 9, wherein the pharmaceutical composition comprises 0.01 to 1.0 w/v % of mometasone furoate, 0.05 to 1.0 w/v % of azelastine hydrochloride, 0.1 to 0.5 w/v % of thaumatin, 1.0 to 5.0 w/v % of a mixture of microcrystalline cellulose and sodium carboxymethyl cellulose, 0.2 to 0.6 w/v % of a mixture of citric acid and sodium citrate, 0.001 to 0.1 w/v % of polyoxyethylene sorbitan monooleate, 5.0 to 10.0 w/v % of a mixture of glycerin and sorbitol, 0.01 to 1.0 w/v % of sodium edentate and 0.002 to 0.05 w/v % of benzalkonium chloride, in an aqueous medium.

14. The method of claim 9, wherein the pharmaceutical composition consists of 0.05 w/v % of mometasone furoate, 0.14 w/v % of azelastine hydrochloride, 0.25 w/v % of thaumatin, 2.0 w/v % of a mixture of microcrystalline cellulose and sodium carboxymethyl cellulose, 0.2 w/v % of citric acid, 0.28 w/v % of sodium citrate, 0.01 w/v % of polyoxyethylene sorbitan monooleate, 2.1 w/v % of glycerin, 6.6 w/v % of sorbitol, 0.1 w/v % of sodium edetate, 0.02 w/v % of benzalkonium chloride and the remaining amount of water.

15. The method of claim 14, wherein the pharmaceutical composition is a nasal spray form.

16. The method of claim 9, wherein the pharmaceutical composition is a nasal spray form.

* * * * *